US007250439B2

(12) United States Patent
Gaines et al.

(10) Patent No.: US 7,250,439 B2
(45) Date of Patent: Jul. 31, 2007

(54) MATRIX METALLOPROTEINASE INHIBITORS

(75) Inventors: Simon Gaines, Stevenage (GB); Ian Peter Holmes, Stevenage (GB); Stephen Paul Watson, Stevenage (GB)

(73) Assignee: Glaxo Group Limited, Greenford Middlesex, ONN (GB)

( * ) Notice: Subject to any disclaimer, the term of this patent is extended or adjusted under 35 U.S.C. 154(b) by 0 days.

(21) Appl. No.: 10/559,600

(22) PCT Filed: Jun. 1, 2004

(86) PCT No.: PCT/EP2004/005966

§ 371 (c)(1),
(2), (4) Date: Dec. 2, 2005

(87) PCT Pub. No.: WO2004/110974

PCT Pub. Date: Dec. 23, 2004

(65) Prior Publication Data

US 2006/0160875 A1    Jul. 20, 2006

(30) Foreign Application Priority Data

Jun. 3, 2003   (GB) ................. 0312654.7

(51) Int. Cl.
*A61K 31/40*   (2006.01)
*C07D 209/46*   (2006.01)
*C07C 315/00*   (2006.01)
*C07C 229/00*   (2006.01)

(52) U.S. Cl. .............. 514/411; 548/472; 562/430; 562/450

(58) Field of Classification Search ........... 514/411; 548/472; 562/430, 450
See application file for complete search history.

(56) References Cited

U.S. PATENT DOCUMENTS 6,350,885 B1   2/2002   O'Brien et al.

FOREIGN PATENT DOCUMENTS

WO    WO 98/09940 A    3/1998

OTHER PUBLICATIONS

Barron, et al., J. Med. Chem., 1968, vol. 11, No. 6, pp. 1139-1144.

Robertson, L.W. et al., Chemical Abstract Service, May 12, 1984, "Microbiological Oxidation of the Pentyl Side Chain of Cannabinoids", Abstract No. XP002302182.
N Miyaura et al., "Palladium-Catalyzed Cross-Coupling Reactions of Organoboron Compounds", Chem. Rev., 1995, 95, 2457-2483.
A. Suzuki, "Recent Advances in the Cross-Coupling Reactions of Organoboron Derivatives with Organic Electrophiles, 1995-1998", J. Oranometallic Chem., 1999, 576, 147-168.

*Primary Examiner*—James Wilson
*Assistant Examiner*—M. Louisa Lao
(74) *Attorney, Agent, or Firm*—Grace C. Hsu; Mary E. McCarthy; Charles Kinzig

(57) ABSTRACT

Compounds of formula (I):

$$R^4-Z-Q-X\underset{R^1\ R^{1'}\ R^3\ R^{3'}}{\overset{Y}{\diagdown\!\diagup\!\diagdown\!\diagup}}R^2 \quad (I)$$

wherein:
Q represents an optionally substituted 5- or 6-membered aryl or heteroaryl ring;
X represents O, S, $NR^5$ or $CR^6 R^7$;
Y represents CHOH, CHSH, $NOR^8$, $CNR^8$ or $CNOR^8$;
Z represents a bond, $CR^{10}R^{11}$, O, S, SO, $SO_2$, $NR^{10}$, $OCR^{10}R^{11}$, $CR^{10}R^{11}$ O or Z,
$R^4$ and Q together form an optionally substituted fused tricyclic group;
$R^1$, $R^{1'}$, $R^3$ and $R^{3'}$ each independently represents H, $C_{1-6}$ alkyl or $C_{1-4}$ alkylaryl;
$R^2$ represents $CO_2R^8$, $CONR^5OR^9$ or $NR^5COR^9$;
$R^4$ represents optionally substituted 5- or 6-membered aryl or heteroaryl;
$R^5$ represents H or $C_{1-3}$ alkyl;
$R^6$ and $R^7$ each independently represents H, $C_{1-3}$ alkyl or halo;
$R^8$ represents H or $C_{1-2}$ alkyl;
$R^9$ represents H or $C_{1-3}$ alkyl;
$R^{10}$ and $R^{11}$ each independently represents H, $C_{1-6}$ alkyl or $C_{1-4}$ alkylaryl; and physiologically functional derivatives thereof, processes for their preparation, pharmaceutical formulations containing them and their use as inhibitors of matrix metalloproteinase enzymes (MMPs) are described.

3 Claims, No Drawings

MATRIX METALLOPROTEINASE INHIBITORS

This invention relates to novel chemical compounds, processes for their preparation, pharmaceutical formulations containing them and their use in therapy.

The compounds of the invention are inhibitors of matrix metalloproteinase enzymes (MMPs).

Matrix metalloproteinase enzymes play a major role in extracellular matrix component degradation and remodelling. Examples of MMPs include collagenase 1, 2 and 3, gelatinase A and B, stromelysin 1, 2 and 3, matrilysin, macrophage metalloelastase, enamelysin and membrane type 1, 2, 3 and 4 MMP. The enzymes are secreted by connective tissue cells and inflammatory cells. Enzyme activation can not only initiate tissue damage but induce increased inflammatory cell infiltration into the tissue, leading to more enzyme production and subsequent tissue damage. For example, elastin fragments produced by MMP degradation are believed to stimulate inflammation by attracting macrophages to the site of MMP activity. Inhibition of MMPs provides a means for treating disease states wherein inappropriate metalloprotease activity results in degradation of connective tissue and inflammation.

In one aspect, the present invention provides compounds of formula (I):

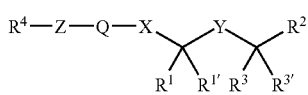

Wherein:
Q represents an optionally substituted 5- or 6-membered aryl or heteroaryl ring;
X represents O, S, $NR^5$ or $CR^6R^7$;
Y represents CHOH, CHSH, $NOR^8$, $CNR^8$ or $CNOR^8$;
Z represents a bond, $CR^{10}R^{11}$, O, S, SO, $SO_2$, $NR^{10}$, $OCR^{10}R^{11}$, $CR^{10}R^{11}O$ or Z, $R^4$ and Q together form an optionally substituted fused tricyclic group;
$R^1$, $R^{1'}$, $R^3$ and $R^{3'}$ each independently represents H, $C_{1-6}$alkyl or $C_{1-4}$ alkylaryl;
$R^2$ represents $CO_2R^8$, $CONR^5OR^9$ or $NR^5COR^9$;
$R^4$ represents optionally substituted 5- or 6-membered aryl or heteroaryl;
$R^5$ represents H or $C_{1-3}$alkyl;
$R^6$ and $R^7$ each independently represents H, $C_{1-3}$alkyl or halo;
$R^8$ represents H or $C_{1-2}$ alkyl;
$R^9$ represents H or $C_{1-3}$ alkyl;
$R^{10}$ and $R^{11}$ each independently represents H, $C_{1-6}$ alkyl or $C_{1-4}$ alkylaryl;
and physiologically functional derivatives thereof, with the exception of 6H-dibenzo[b,d]pyran-3-pentanoic acid (1-dihydroxy-6,6,9-trimethyl), with the provisos that:
when Q represents phenyl; X is O, S or $CR^6R^7$ where $R^6$ and $R^7$ each independently represents H or $C_{1-3}$ alkyl; Z represents a bond, $C_{2-4}$alkylene, S, SO, $SO_2$, $OCH_2$ or $CH_2O$; and Y represents CHOH, $R^4$ does not represent phenyl substituted in the ortho position by a substituent X'W' wherein X' is —$NR^1C(O)NR^2$—, —$NR^1C(O)$—, —$NR^1C(O)O$—, —$C(O)NR^2$—, or —$OC(O)NR^2$— (wherein $R^1$ and $R^2$ are independently selected from hydrogen, $C_{1-4}$ alkyl and $C_{1-4}$ haloalkyl) and W' is hydrogen or a $C_{1-12}$hydrocarbyl group optionally substituted by one or more groups independently selected from hydrogen, $C_{1-4}$ alkyl, $C_{1-4}$ alkoxy, hydroxy, $C_{1-4}$ haloalkyl and $C_{1-4}$ haloalkoxy; and when $R^4$, Z and Q together form a group

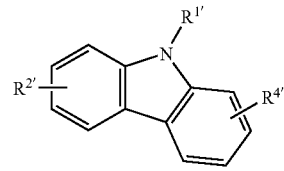

wherein $R^{1'}$ is H, $C_{1-6}$ alkyl, $C_{1-4}$ alkoxy$C_{1-4}$ alkyl, $C_{1-6}$ alkanoyl, $C_{1-4}$ alkanoyl$C_{1-4}$ alkyl, aryl, aryl$C_{1-4}$ alkyl, aryl-$C_{1-4}$ alkoxy$C_{1-4}$ alkyl, aryl$C_{1-4}$ alkanoyl, arylcarbonyl, heteroaryl, heteroaryl $C_{1-4}$ alkyl, heteroaryl$C_{1-4}$ alkoxy $C_{1-4}$ alkyl, heteroaryl$C_{1-4}$ alkanoyl, heteroarylcarbonyl, heterocyclyl, heterocyclyl$C_{1-4}$ alkyl, heterocyclyl$C_{1-4}$ alkoxy$C_{1-4}$ alkyl, heterocyclyl$C_{1-4}$ alkanoyl, heterocyclylcarbonyl, carbocyclyl, carbocyclyl$C_{1-4}$ alkyl, carbocyclyl$C_{1-4}$ alkoxy$C_{1-4}$ alkyl, carbocyclyl$C_{1-4}$ alkanoyl, carbocyclylcarbonyl, $C_{1-4}$ alkylsulphonyl, N,N-di-$C_{1-4}$ alkylaminosulphonyl or N—$C_{1-4}$ alkylaminosulphonyl wherein $R^{1'}$ may be optionally substituted by up to three substituents independently selected from $C_{1-4}$ alkyl optionally substituted by up to three fluro substituents, $C_{1-4}$ alkoxy, $C_{1-4}$alkanoyl, carboxy, hydroxy, halo, cyano, amino, N—$C_{1-4}$ alkylamino, N,N-di-$C_{1-4}$ alkylamino, $C_{1-4}$ alkanoylamino, mercapto, $C_{1-4}$ alkylsulphonyl, $C_{1-4}$ alkylsulphinyl, $C_{1-4}$ alkylsulphanyl, nitro, heteroaryl$C_{1-4}$ alkanoylamino, or $C_{1-4}$alkoxycarbonyl;

$R^{2'}$ is selected from hydrogen, $C_{1-4}$alkyl (optionally substituted by hydroxy), $C_{1-4}$alkoxy, cyano, nitro, halo, amino, N—$C_{1-4}$alkylamino, or N,N-di-alkylamino; and
$R^{4'}$ is selected from hydrogen, $C_{1-4}$alkyl, halo or nitro;
X is NH or $CR^6R^7$; and
Y is CHOH;
$R^2$ is not $CO_2R^8$ wherein $R^8$ is $C_{1-2}$alkyl.

References to 'aryl' include references to monocyclic carbocyclic aromatic rings (e.g. phenyl) and bicyclic carbocyclic aromatic rings (e.g. naphthyl) and references to 'heteroaryl' include references to mono- and bicyclic heterocyclic aromatic rings containing 1–3 hetero atoms selected from nitrogen, oxygen and sulphur. Examples of monocyclic heterocyclic aromatic rings include e.g. pyridinyl, pyrimidinyl, thiophenyl, furanyl, pyrrolyl, oxazolyl, isoxazolyl, oxadiazolyl, thiazolyl, thiadiazolyl or imidazolyl, and examples of bicyclic heterocyclic aromatic rings include e.g. benzimidazolyl, quinolinyl or indolyl. Carbocyclic and heterocyclic aromatic rings may be optionally substituted, e.g. by one or more $C_{1-6}$ alkyl, $C_{2-6}$ alkenyl, halogen, $(CH_2)_{0-4}OR^6$, $(CH_2)_{0-4}SR^6$, $SO_2R^6$, $COR^6$, aryloxy, thioaryl, cyano, hydroxy, nitro, $NR^6R^7$, —$NR^6COR^7$, —$OCF_3$, —$CF_3$, $COOR^7$, —$OCHCF_2$, —$SCF_3$, —$CONR^6R^7$—$SO_2NR^6R^7$, or like groups.

References to alkyl include references to both straight chain and branched chain aliphatic isomers of the corresponding alkyl. It will be appreciated that references to alkylene and alkoxy shall be interpreted similarly.

Preferably, $R^1$ and $R^{1'}$ each represents hydrogen.
Preferably $R^2$ represents $CO_2R^8$, more preferably $CO_2H$.
Preferably $R^3$ and $R^{3'}$ each represents hydrogen.
Preferably $R^4$ represents optionally substituted phenyl or heteroaryl.

Preferably X represents $CH_2$.

Preferably Y represents CHOH.

Preferably Z represents a bond, or Z, $R^4$ and Q together represent a fused tricyclic group.

A preferred subgroup of compounds of formula (I) is presented by formula (Ia):

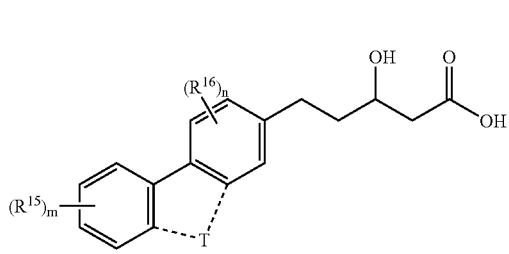

wherein:

T is absent or represents O, S, $NR^{17}$ or $CR^{17}R^{18}$;

— represents optional bonds;

$R^{15}$ and $R^{16}$ each independently represents halo, cyano, nitro, $OR^{17}$, $SR^{17}$, $COR^{17}$, $NR^{18}COR^{17}$, $CONR^{17}R^{18}$, optionally substituted phenoxy or $C_{1-6}$ alkyl optionally substituted by $OR^{17}$;

$R^{17}$ represents H, $C_{1-6}$ alkyl or $C_{1-4}$ alkylaryl;

$R^{18}$ represents H or $C_{1-6}$ alkyl;

m and n each independently represents 0 or an integer 1, 2 or 3;

with the proviso that when T is absent, $R^{15}$ does not represent $NR^{18}COR^{17}$ or $CONR^{17}R^{18}$ in the ortho position; and physiologically functional derivatives thereof.

Preferably n is 0 and m is 1.

Preferably $R^{15}$ represents a para-substituent selected from $NO_2$, $C_{1-6}$ alkyl, $C_{1-6}$ alkoxy, halo, $SC_{1-6}$ alkyl, CN or $COC_{1-6}$ alkyl.

By the term "physiologically functional derivative" is meant a chemical derivative of a compound of formula (I) having the same physiological function as the free compound of formula (I), for example, by being convertible in the body thereto and includes any pharmaceutically acceptable esters, amides and carbamates, salts and solvates of compounds of formula (I) which, upon administration to the recipient, are capable of providing (directly or indirectly) compounds of formula (I) or active metabolite or residue thereof.

Suitable salts of the compounds of formula (I) include physiologically acceptable salts and salts which may not be physiologically acceptable but may be useful in the preparation of compounds of formula (I) and physiologically acceptable salts thereof. If appropriate, acid addition salts may be derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, palmoates, methanesulphonates, formates or trifluoroacetates.

Examples of solvates include hydrates.

When compounds of formula (I) contain chiral centres, the invention extends to mixtures of enantiomers (including racemic mixtures) and diastereoisomers as well as to individual enantiomers. Generally it is preferred to use a compound of formula (I) in the form of a purified single enantiomer.

The compounds of formula (I) and salts and solvates thereof may be prepared by the methodology described hereinafter, constituting a further aspect of this invention.

A first process (A) according to the invention for preparing a compound of formula (I) wherein Z represents a bond comprises reacting a compound of formula (II):

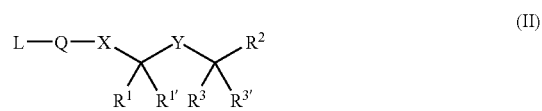

wherein $R^1$, $R^{1'}$, $R^2$, $R^3$, $R^{3'}$, Q, X and Y are as previously defined for formula (I) and L represents a leaving group, with a reagent suitable to introduce the group $R^4Z$, such as a compound $R^4ZB(OH)_2$, suitably in the presence of a catalyst, such as a nobel metal catalyst e.g. palladium, and a suitable base, such as an alkali metal carbonate, e.g. caesium carbonate. The reaction is conveniently carried out in a suitable solvent, such as a polar organic solvent, e.g. dimethyl formamide. Suitable leaving groups represented by L include halides, especially bromide or iodide.

An alternative process (B), for the preparation of compounds of formula (I) wherein Y represents NOH comprises oxidation of a compound of formula (III):

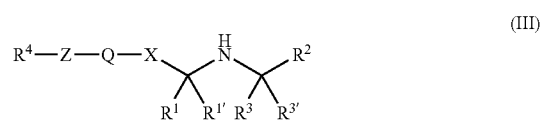

wherein $R^4$, Z, Q, X, $R^1$, $R^{1'}$, $R^3$, $R^{3'}$ and $R^2$ are as previously defined for formula (I). Suitable oxidising agents include meta-chloroperbenzoic acid or t-butylhydroperoxide in a suitable solvent such as dichloromethane or toluene. The reaction is suitably conducted at ambient temperature, such as about 18–25° C.

A further alternative process, (C), for the preparation of compounds of formula (I) wherein X represents O or S and Y represents CHOH comprises reaction of a compound of formula (IV):

wherein $R^4$, Z and Q are as previously defined for formula (I) and X represents O or S with a compound of formula (VA) or (VB):

wherein $R^1$, $R^{1'}$, $R^3$, $R^{3'}$ and $R^2$ are as previously defined for formula (I) and L is a leaving group, in the presence of a base, followed, if necessary, by reduction. Suitable bases include alkali metal alkoxides, such as potassium t-butoxide, in a suitable solvent such as dimethylformamide at a temperature of about 15–50° C. Suitable leaving groups represented by L include halides, especially bromides and iodides. Suitable reducing agents will be readily apparent to those skilled in the art and included, for example, sodium borohydride.

It will be appreciated by those skilled in the art that compounds of formula (I) may also be prepared from other compounds of formula (I) by interconversion using processes such as oxidation, reduction, substitution, deprotection etc., standard in the art of synthetic chemistry.

Compounds of formula (II) wherein X is $CR^6R^7$ wherein $R^6$ and $R^7$ each independently represents H or $C_{1-3}$ alkyl may be prepared by reaction of compounds of formula (VI):

wherein L and Q are as defined for formula (II), X is $CR^6R^7$ wherein $R^6$ and $R^7$ each independently represents H or $C_{1-3}$ alkyl and $L^2$ represents a leaving group more labile than L, with a compound of formula (X)

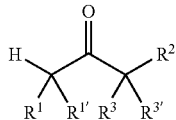

wherein $R^1$, $R^{1'}$, $R^2$, $R^3$ and $R^{3'}$ are as previously defined for formula (I) in the presence of a suitable base. Suitable bases include alkali metal hydrides, such as sodium hydride, and alkyl lithiums such as n-butyl lithium. The reaction is suitably conducted in a anhydrous organic solvent, such as tetrahydrofuran, at low temperature, such as about 0° C. Other compounds of formula (II) are commercially available or may be obtained from commercially available compounds via procedures well know to those skilled in the art.

Compounds of formula (III) may be prepared by reaction of compounds of formula (VII):

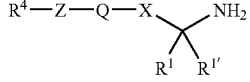

wherein $R^4$, Z, Q, X, $R^1$ and $R^{1'}$ are as previously defined for formula (I) with compounds of formula (VIII):

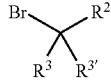

wherein $R^2$, $R^3$ and $R^{3'}$ are as previously defined for formula (I) in the presence of a base, such as an alkali metal alkoxide, e.g. potassium butoxide, in a suitable organic solvent, such as dimethyl formamide.

Compounds of formula (IV), (VII) and (IX) are known or may be prepared by known methods, such as those described by N Miyaura and A Suzuki in Chem. Rev., 1995, 95, 2457–2483 and A. Suzuki in J. Oranometallic Chem., 1999, 576, 147–168.

Compounds of formula (VA), (VB), (VIII) and (X) are known or may be prepared from known compounds by methods familiar to those skilled in the art. For example, epoxides of formula (VA) may be prepared from the corresponding alkenes via oxidation, for example, using meta-chloroperbenzoic acid.

The enantiomeric compounds of the invention may be obtained (a) by the separation of the components of the corresponding racemic mixture, for example, by chiral chromatography, enzymatic resolution methods or preparing and separating suitable diastereolsomers, (b) by direct synthesis from the appropriate chiral starting materials by the methods described above, or (c) by methods analogous to those described above using chiral reagents.

Optional conversion of a compound of formula (I) to a corresponding salt may conveniently be effected by reaction with the appropriate acid or base. Optional conversion of a compound of formula (I) to a corresponding solvate or other physiologically functional derivative may be effected by methods known to those skilled in the art.

Compounds of formula (I) may be useful for the treatment of any conditions in which inhibition of matrix metalloproteinase would be beneficial, especially in the treatment of inflammatory diseases and autoimmune disorders.

Examples of inflammatory conditions and autoimmune disorders in which the compounds of the invention have potentially beneficial effects include diseases of the respiratory tract such as asthma (including allergen-induced asthmatic reactions), cystic fibrosis, bronchitis (including chronic bronchitis), chronic obstructive pulmonary disease (COPD), adult respiratory distress syndrome (ARDS), chronic pulmonary inflammation, rhinitis and upper respiratory tract inflammatory disorders (URID), ventilator induced lung injury, silicosis, pulmonary sarcoidosis, idiopathic pulmonary fibrosis, bronchopulmonary dysplasia, arthritis, e.g. rheumatoid arthritis, osteoarthritis, infectious arthritis, psoriatic arthritis, traumatic arthritis, rubella arthritis, Reiter's syndrome, gouty arthritis and prosthetic joint failure, gout, acute synovitis, spondylitis and non-articular inflammatory conditions, e.g. herniated/ruptured/prolapsed intervertebral disk syndrome, bursitis, tendonitis, tenosynovitic, fibromyalgic syndrome and other inflammatory conditions associated with ligamentous sprain and regional musculoskeletal strain, inflammatory disorders of the gastrointestinal tract, e.g. ulcerative colitis, diverticulitis, Crohn's disease, inflammatory bowel diseases, irritable bowel syndrome and gastritis, multiple sclerosis, systemic lupus erythematosus, scleroderma, autoimmune exocrinopathy, autoimmune encephalomyelitis, diabetes, tumor angiogenesis and metastasis, cancer including carcinoma of the breast, colon, rectum, lung, kidney, ovary, stomach, uterus, pancreas, liver, oral, laryngeal and prosiate, meianoma, acute and chronic leukemia, periodontal disease, neurodegenerative disease, Alzheimer's disease, Parkinson's disease, epilepsy, muscle degeneration, inguinal hernia, retinal degeneration, diabetic retinopathy, macular degeneration, ocular inflammation, bone resorption diseases, osteoporosis, osteopetrosis, graft vs. host reaction, allograft rejections, sepsis, endotoxemia, toxic shock syndrome, tuberculosis, usual interstitial and cryptogenic organizing pneumonia, bacterial meningitis, systemic cachexia, cachexia secondary to infection or malignancy, cachexia secondary to acquired immune deficiency syndrome (AIDS), malaria, leprosy, leishmaniasis, Lyme disease, glomerulonephritis, glomerulosclerosis, renal fibrosis, liver fibrosis, pancreatitis, hepatitis, endometriosis, pain, e.g. that associated with inflammation and/or trauma, inflammatory diseases of the skin, e.g. dermatitis, dermatosis, skin ulcers, psoriasis, eczema, systemic vasculitis, vascular dementia, thrombosis, atherosclerosis, restenosis, reperfusion injury, plaque calcification, myocarditis, aneurysm, stroke, pulmonary hypertension, left ventricular remodeling and heart failure.

Diseases of principal interest include COPD and inflammatory diseases of the respiratory tract and joints and vascular diseases.

It will be appreciated by those skilled in the art that reference herein to treatment extends to prophylaxis as well as the treatment of established conditions.

There is thus provided as a further aspect of the invention a compound of formula (I) or a physiologically acceptable derivative thereof for use in medicine.

According to another aspect of the invention, there is provided the use of a compound of formula (I) or a physiologically acceptable derivative thereof for the manufacture of a medicament for the treatment of inflammatory conditions or autoimmune disorders.

In a further or alternative aspect there is provided a method for the treatment of a human or animal subject suffering from or susceptible to an autoimmune disorder or an inflammatory condition which method comprises administering to said human or animal subject an effective amount of a compound of formula (I) or a physiologically functional derivative thereof.

The compounds according to the invention may be formulated for administration in any convenient way, and the invention therefore also includes within its scope pharmaceutical compositions comprising a compound of formula (I) or a physiologically acceptable derivative thereof together, if desirable, with one or more physiologically acceptable diluents or carriers.

There is also provided a process for preparing such a pharmaceutical formulation which comprises mixing the ingredients.

The compounds according to the invention may, for example, be formulated for oral, inhaled, intranasal, topical, buccal, parenteral or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compounds according to the invention for topical administration may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

Lotions may be formulated with an aqueous or oily base and will in general also contain one or more emulsifying agents, stabilising agents, dispersing agents, suspending agents, thickening agents, or colouring agents. They may also contain a preservative.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The pharmaceutical compositions according to the invention may also be used in combination with other therapeutic agents, for example anti-inflammatory agents (such as corticosteroids (e.g. fluticasone propionate, beclomethasone dipropionate, mometasone furoate, triamcinolone acetonide or budesonide) or NSAIDs (e.g. sodium cromoglycate, nedocromil sodium, PDE-4 inhibitors, leukotriene antagonists, CCR-3 antagonists, iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof) or antiinfective agents (e.g. antibiotics, antivirals).

It will be appreciated that when the compounds of the present invention are administered in combination with other therapeutic agents normally administered by the inhaled or intranasal route, that the resultant pharmaceutical composition may be administered by the inhaled or intranasal route.

Compounds of the invention may conveniently be administered in amounts of, for example, 0.01 to 100 mg/kg body weight, preferably 0.1 to 25 mg/kg body weight, more preferably 0.3 to 5 mg/kg body weight. The compounds may be given more than once daily to be equivalent to the total daily dose. The precise dose will of course depend on the age and condition of the patient and the particular route of administration chosen and will ultimately be at the discretion of the attendant physician.

No toxicological effects are expected when a compound according to the present invention is administered in the above mentioned dose range.

Compounds of the invention may be tested for in vitro activity in accordance with the following assay:

The fluorescent peptide substrate used in the MMP-12 assay is FAM-Gly-Pro-Leu-Gly-Leu-Phe-Ala-Arg-Lys (TAMRA), where FAM represents carboxyfluorescein, and TAMRA represents tetramethylrhodamine. MMP12 catalytic domain (residues 106–268) protein was expressed in *E. coli* in the form of insoluble inclusion bodies & stored in concentrated solution under denaturing conditions (8M guanidine hydrochloride). Enzyme was refolded into active form in situ by direct dilution into assay reactions. The 51 uL reactions are run in NUNC-brand black,square 384-well plates, each well containing 2 uM substrate, 20 nM enzyme, and 0.001–100 uM inhibitor, in 50 mM HEPES, pH 7.5, 150 mM NaCl, 10 mM CaCl2, 1 uM ZnAc, 0.6 mM CHAPS, and 2% DMSO. Postitive control wells contain no inhibitor. Negative control wells are effected by either pre-dispensing the EDTA quench (see below) or by omiting enyme. Reactions are incubated at ambient temperature for 120 min, then quenched by the addition of 15 uL of 100 mM EDTA. Product formation in each well is quantified by measuring flourescense with a Molecular Devices Acquest. The excitation wavelength is set at 485 nM, and the emmision wavelenght is 530 nM. $IC_{50}$ values were obtained by first calculating the percent inhibition (% I) at each inhibitor concentration (% I=100*(1−(I−C2)/(C1−C2)), where C1 is the mean of the positive controls, and C2 is the mean of the negative controls), then fitting the % I vs. inhibitor concentration [I] data to: % I=A+((B−A)/(1+((C/[I]^D))), where A is the lower asymptote, B is the upper asymptote, C is the IC50 value, and D is the slope factor. When tested in this assay, compounds of Examples 6–28 had IC50s below 100 micromolar.

The invention may be illustrated by reference to the following examples, which should not be construed as a limitation thereto:

General Experimental Details

LC/MS data were obtained under the following conditions:

Column: 3.3cm×4.6 mm ID, 3 um ABZ+PLUS

Flow Rate: 3 ml/min

Injection Volume: 5 μl

Temp: RT

UV Detection Range: 215 to 330 nm

Solvents: A: 0.1% Formic Acid+10 mMolar Ammonium Acetate.

B: 95% Acetonitrile+0.05% Formic Acid

| Gradient: | | |
| --- | --- | --- |
| Time | A% | B% |
| 0.00 | 100 | 0 |
| 0.70 | 100 | 0 |
| 4.20 | 0 | 100 |
| 5.30 | 0 | 100 |
| 5.50 | 100 | 0 |

¹HNMR spectra were obtained at 400 MHz on a Bruker-Spectrospin Ultrashield 400 spectrophotometer.

EXAMPLE 1

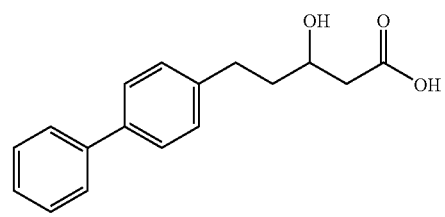

5-Biphenyl-4-yl-3-hydroxy-pentanoic acid

A solution of trifluoroacetic acid in dichloromethane (20%; 10 mL) was added to 5-biphenyl-4-yl-3-hydroxy-pentanoic acid tert-butyl ester (Intermediate 3, 244 mg, 0.748 mmol) and the resulting solution stirred at room temperature for 45 minutes. The volatiles were evaporated under reduced pressure to give the title compound 5 (189 mg, 94%) as a white solid.

LC/MS: 3.24 min; z/e 271, calcd (M+1) 271. ¹H NMR (400 MHz: DMSO-$d_6$): 7.65 (2 H), 7.55 (2 H), 7.43 (2 H), 7.31 (3 H), 4.79 (1 H), 3.85 (1 H), 2.70 (2 H), 2.35 (2 H), 1.71 (2 H).

EXAMPLE 2

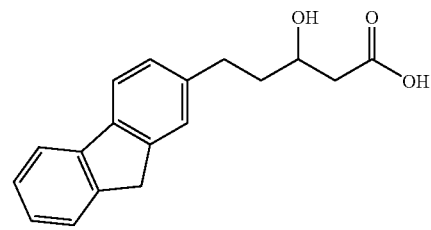

5-(9H-Fluoren-2-yl)-3-hydroxy-pentanoic acid

Prepared analogously to Example 1. LC/MS: 3.22 min; z/e 281, calcd (M−1) 281.

EXAMPLE 3

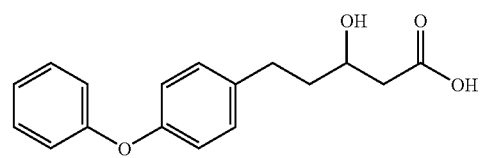

3-Hydroxy-5-(4-phenoxy-phenyl)-pentanoic acidz/e 285, calcd (M−1) 285.

EXAMPLE 4

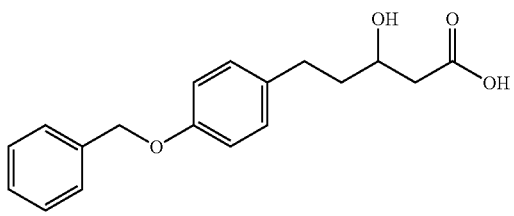

5-(4-Benzyloxy-phenyl)-3-hydroxy-pentanoic acid

Prepared analogously to Example 1. LC/MS: 3.08 min; z/e 299, calcd (M−1) 299.

EXAMPLE 5

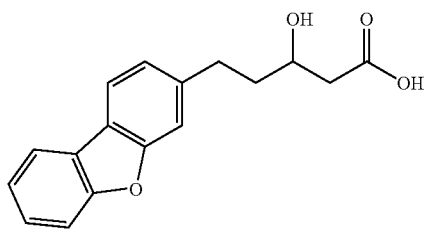

5-Dibenzofuran-3-yl-3-hydroxy-pentanoic acid

Prepared analogously Example 1. LC/MS: 3.22 min; z/e 283, calcd (M−1) 283.

EXAMPLE 6

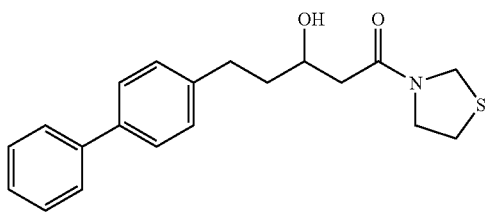

5-Biphenyl-4-yl-3-hydroxy-1-thiazolidin-3-yl-pentan-1-one

Diisopropylethylamine (32 μL, 0.19 mmol) was added to a stirred solution of 5-biphenyl-4-yl-3-hydroxy-pentanoic acid (Example 1, 25 mg, 93 μmol) and O-(7-azabenzotriazol-1-yl)-N,N,N',N'-tetramethyluronium hexafluorophosphate (70 mg, 0.19 mmol) in dimethylformamide (1 mL) at room temperature under nitrogen. After stirring for 5 minutes, thiazolidine (11 μL, 0.14 mmol) was added then stirring was continued for a further 2 hours. The volatiles were removed by evaporation under reduced pressure and the residue partitioned between dichloromethane (5 mL) and water (5 mL). The phases were separated and the organic phase evaporated under reduced pressure. The residue was purified by column chromatography on silica gel (1:1 ethyl acetate: 40–60 petroleum ether) to give the title compound (15 mg, 47%) as a white solid. LC/MS: 3.22 min; z/e 342, calcd (M+1) 342.

$^1$H NMR (400 MHz: CDCl$_3$): 7.59 (2 H), 7.51 (2 H), 7.42 (2 H), 7.30 (3 H), 4.57, 4.42. 4.12, 3.85, 3.68, 3.09, 3.01, 2.90. 2.76, 2.47 (2 H), 1.93 (1 H), 1.78 (1 H).

EXAMPLE 7

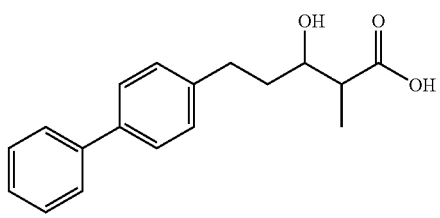

5-Biphenyl-4-yl-3-hydroxy-2-methyl-pentanoic acid

A solution of trifluoroacetic acid in dichloromethane (20%; 10 mL) was added to 5-biphenyl-4-yl-2-methyl-3-oxo-pentanoic acid tert-butyl ester (Intermediate 7, 130 mg, 0.382 mmol) and the resulting solution stirred at room temperature for 1.5 hour. The volatiles were evaporated under reduced pressure and the residue was purified by column chromatography on silica gel (1:2 ethyl acetate: 40–60 petroleum ether) to give the title compound (60 mg, 56%) as a white solid, mixture of diastereoisomers. LC/MS: 3.22 min; z/e 302, calcd (M+NH$_4$) 302. $^1$H NMR (400 MHz: CDCl$_3$): 7.59 (2 H), 7.51 (2 H), 7.40 (2 H), 7.28 (3 H), 4.21, 4.01 3.75, 2.91, 2.76, 2.62, 1.88, 1.25.

EXAMPLE 8

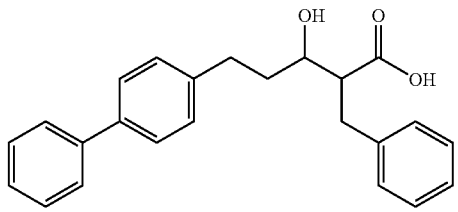

2-Benzyl-5-biphenyl-4-yl-3-hydroxy-pentanoic acid

Prepared analogously to Example 7, mixture of diastereoisomers. LC/MS: 3.54 min and 3.61 min; z/e 378, calcd (M+NH$_4$) 378.

EXAMPLE 9

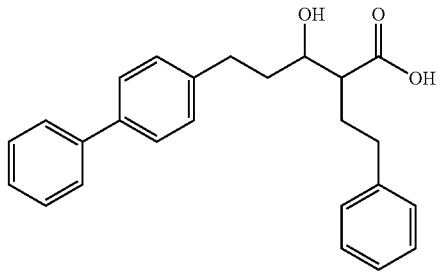

5-Biphenyl-4-yl-3-hydroxy-2-phenethyl-pentanoic acid

Prepared analogously to Example 7, mixture of diastereoisomers. LC/MS: 3.59 min and 3.66 min; z/e 373, calcd (M−1) 373.

EXAMPLE 10

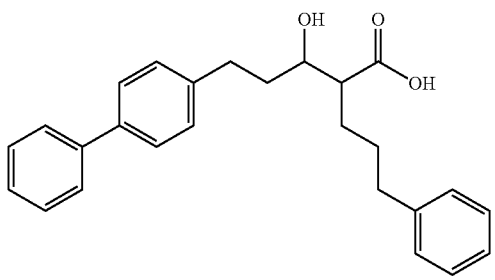

5-Biphenyl-4-yl-3-hydroxy-2-(3-phenyl-propyl)-pentanoic acid

Prepared analogously to Example 7, mixture of diastereoisomers. LC/MS: 3.71 min and 3.79 min; z/e 387, calcd (M−1) 387.

EXAMPLE 11

Biphenyl-4-yl-3-hydroxy-pentanoic acid—enantiomer 1

A racemic sample of 5-biphenyl-4-yl-3-hydroxy-pentanoic acid (Example 1) was resolved using preparative chiral HPLC (Chiralpak-AD column, 15% ethanol:heptane (0.1% trifluoroacetic acid), 15 mL/min) 13.5 min.

Example 12

Biphenyl-4-yl-3-hydroxy-pentanoic acid—enantiomer 2

A racemic sample of 5-biphenyl4-yl-3-hydroxy-pentanoic acid (Example 1) was resolved using preparative chiral HPLC (Chiralpak-AD column, 15% ethanol:heptane (0.1% trifluoroacetic acid), 15 mL/min) 15.2 min.

EXAMPLE 13

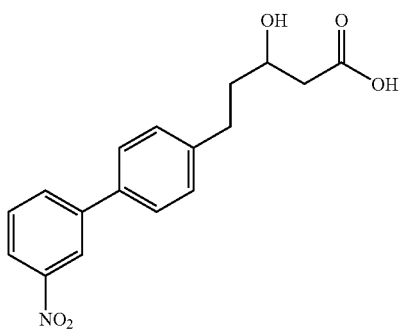

3-Hydroxy-5-(3'-nitro-biphenyl-4-yl)-pentanoic acid

3-Hydroxy-5-(4iodo-phenyl)-pentanoic acid (Intermediate 10, 16 mg, 50 μmol), cesium carbonate (40 mg, 125 μmol), 3-nitrophenylboronic acid (10 mg, 60 μmol) and FibreCat™ 1001 (20 mg, 2.7% w/w palladium) were suspended in dimethylformamide (200 μL) and then heated at 100° C. for 1 hour. The reaction was cooled to room temperature and the solvent removed under reduced pressure. The residue was partitioned between 10% methanol/dichloromethane and 2 M HCl then the phases separated. The organic phase was evaporated under reduced pressure and the residue purified via mass directed HPLC to give the title compound (5 mg, 32%) as a white solid. LC/MS: 3.18 min; z/e 314, calcd (M−1) 314. $^1$H NMR (400 MHz: DMSO-d6): 8.4 (1 H), 8.15 (2 H), 7.7 (3 H), 7.35 (2 H), 3.85 (1 H), 2.7 (2 H), 2.32 (2 H), 1.7 (2 H).

EXAMPLE 14

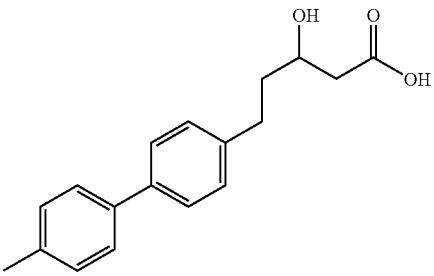

3-Hydroxy-5-(4'-methyl-biphenyl-4-yl)-pentanoic acid

Prepared analogously to Example 13. LC/MS: 3.43 min; z/e 283, calcd (M−1) 283.

EXAMPLE 15

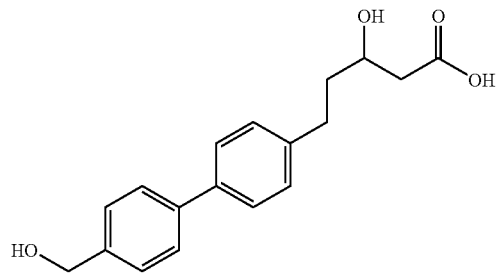

3-Hydroxy-5-(4'-hydroxymethyl-biphenyl-4-yl)-pentanoic acid

Prepared analogously to Example 13. LC/MS: 2.71 min; z/e 299, calcd (M−1) 299.

EXAMPLE 16

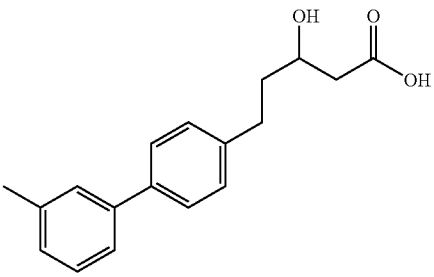

3-Hydroxy-5-(3'-methyl-biphenyl-4-yl)-pentanoic acid

Prepared analogously to Example 13. LC/MS: 3.36 min; z/e 283, calcd (M−1) 283.

EXAMPLE 17

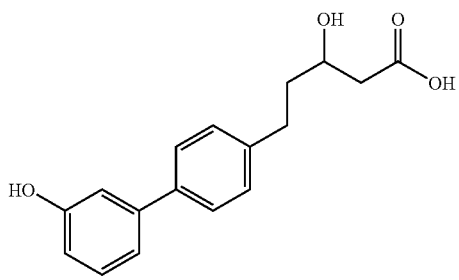

3-Hydroxy-5-(3'-hydroxy-biphenyl-4-yl)-pentanoic acid

Prepared analogously to Example 13. LC/MS: 2.86 min; z/e 285, calcd (M−1) 285.

EXAMPLE 18

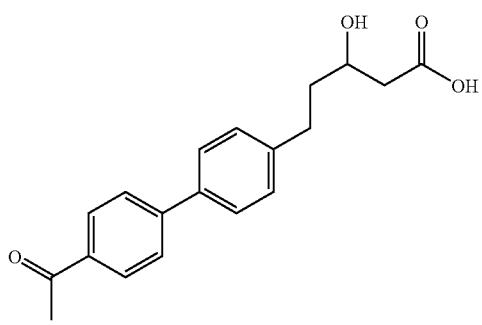

5-(4'-Acetyl-biphenyl-4-yl)-3-hydroxy-pentanoic acid

Prepared analogously to Example 13. LC/MS: 3.02 min; z/e 311, calcd (M−1) 311.

EXAMPLE 19

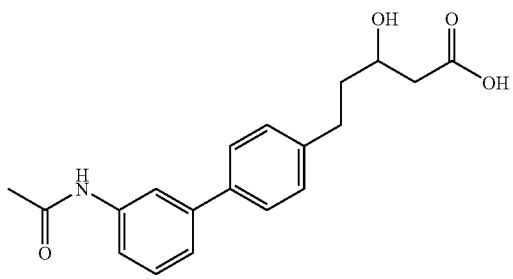

5-(3'-Acetylamino-biphenyl-4-yl)-3-hydroxy-pentanoic acid

Prepared analogously to Example 13. LC/MS: 2.71 min; z/e 326, calcd (M−1) 326.

EXAMPLE 20

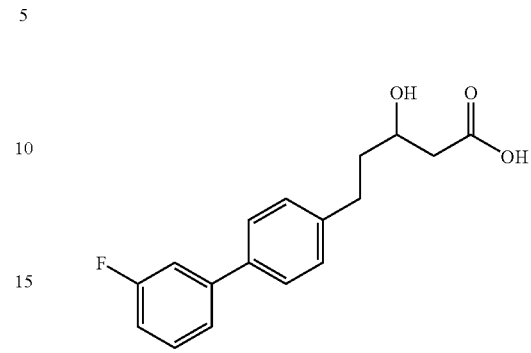

5-(3'-Fluoro-biphenyl-4-yl)-3-hydroxy-pentanoic acid

Prepared analogously to Example 13. LC/MS: 3.27 min; z/e 287, calcd (M−1) 287.

EXAMPLE 21

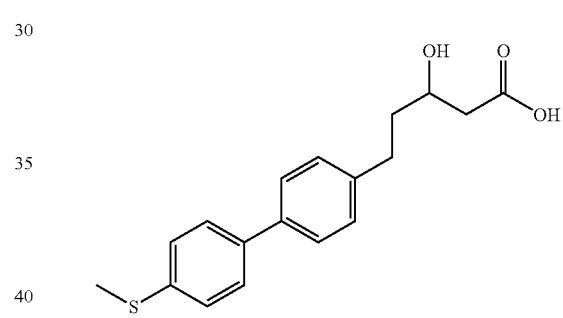

3-Hydroxy-5-(4'-methylsulfanyl-biphenyl-4-yl)-pentanoic acid

Prepared analogously to Example 13. LC/MS: 3.44 min; z/e 315, calcd (M−1) 315.

EXAMPLE 22

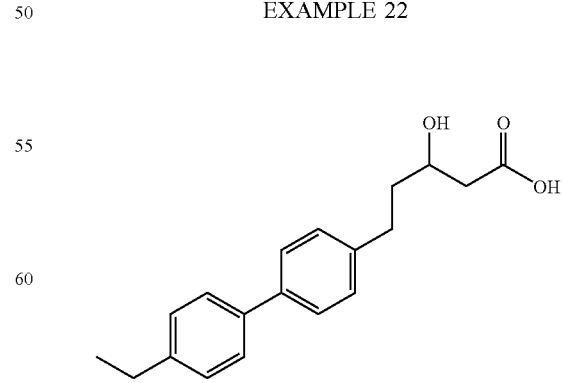

5-(4'-Ethyl-biphenyl-4-yl)-3-hydroxy-pentanoic acid

Prepared analogously to Example 13. LC/MS: 3.60 min; z/e 297, calcd (M−1) 297.

EXAMPLE 23

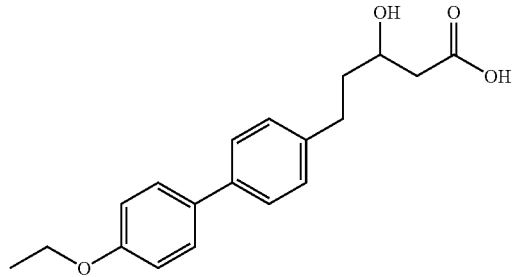

5-(4'-Ethoxy-biphenyl-4-yl)-3-hydroxy-pentanoic acid

Prepared analogously to Example 13. LC/MS: 3.40 min; z/e 313, calcd (M−1) 313.

EXAMPLE 24

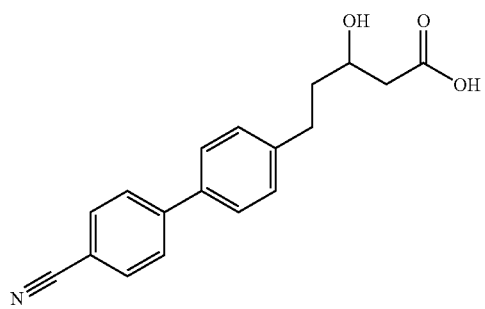

5-(4'-Cyano-biphenyl-4-yl)-3-hydroxy-pentanoic acid

Prepared analogously to Example 13. LC/MS: 3.08 min; z/e 294, calcd (M−1) 294.

EXAMPLE 25

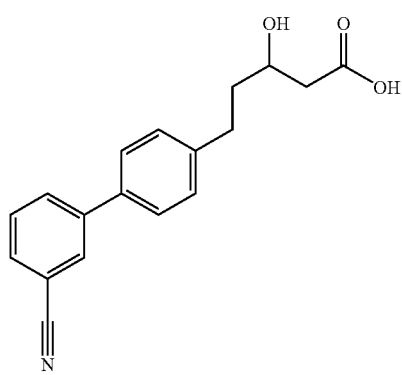

5-(3'-Cyano-biphenyl-4-yl)-3-hydroxy-pentanoic acid

Prepared analogously to Example 13. LC/MS: 3.05 min; z/e 294, calcd (M−1) 294.

EXAMPLE 26

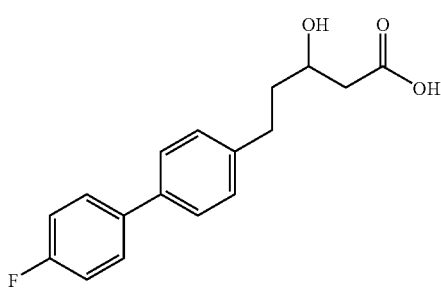

5-(4'-Fluoro-biphenyl-4-yl)-3-hydroxy-pentanoic acid

Prepared analogously to Example 13. LC/MS: 3.26 min; z/e 287, calcd (M−1) 287.

EXAMPLE 27

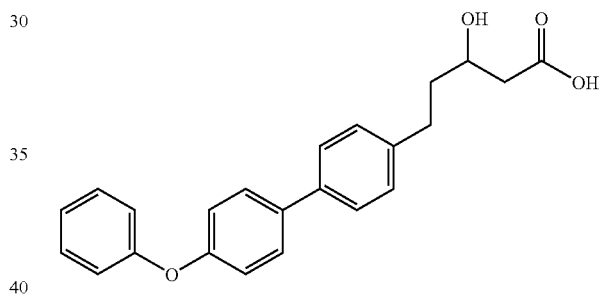

3-Hydroxy-5-(4'-phenoxy-biphenyl-4-yl)-pentanoic acid

Prepared analogously to Example 13. LC/MS: 3.73 min; z/e 361, calcd (M−1) 361.

EXAMPLE 28

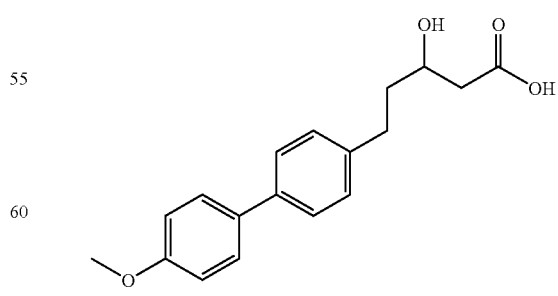

3-Hydroxy-5-(4'-methoxy-biphenyl-4-yl)-pentanoic acid

Prepared analogously to Example 13. LC/MS: 3.19 min; z/e 299, calcd (M−1) 299.

Intermediate 1

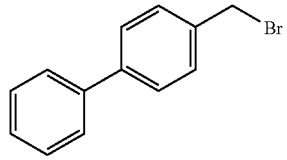

4-Bromomethyl-biphenyl

Carbon tetrabromide (8.99 g, 27.1 mmol) and triphenyl phosphine (7.11 g, 27.1 mmol) were added to a stirred solution of biphenyl-4-yl methanol (5.00 g, 27.1 mmol) in dichloromethane (100 mL) at room temperature. Stirring was continued at room temperature for 1.5 hours then the solvent removed by evaporation under reduced pressure. The residue was purified by column chromatography on silica gel (1:20 diethyl ether:cyclohexane) to give the title compound (6.37 g, 95%) as a white solid. $^1$H NMR (400 MHz: CDCl$_3$): 7.6 (4 H), 7.45 (4 H), 7.35 (1 H), 4.55 (2 H).

Intermediate 2

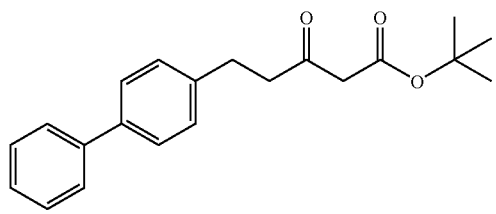

5-Biphenyl-4-yl-3-oxo-pentanoic acid tert-butyl ester

A solution of t-butyl acetoaceate (1.84 mL, 11.1 mmol) in tetrahydrofuran (20 mL) was added to a stirred suspension of sodium hydride (488 mg, 12.2 mmol) in tetrahydrofuran (10 mL) at 0° C. under nitrogen. After stirring for 10 minutes n-butyl lithium (1.6 M in hexanes; 7.3 mL, 11.6 mmol) was added dropwise over 2 minutes then stirring was continued for a further 10 minutes. A solution of 4-bromomethyl-biphenyl (Intermediate 1, 3.00 g, 12.2 mmol) in tetrahydrofuran (6 mL) was added dropwise over 10 minutes and the resulting solution stirred at 0° C. for 1.5 hours. 6 M Hydrochloric acid (15 mL) was added then the crude reaction mixture was extracted with diethyl ether (3×50 mL). The organic phases were combined, washed with brine (50 mL), dried (MgSO$_4$) then the solvent evaporated under reduced pressure. The residue was purified by column chromatography on silica gel (1:20 diethyl ether:cyclohexane) to give the title compound (1.37 g, 38%) as a yellow solid. LC/MS: 3.78 min; z/e 342, calcd (M+NH$_4$) 342. $^1$H NMR (400 MHz: CDCl$_3$): 7.55 (2 H), 7.50 (2 H), 7.43 (2 H), 7.32 (1 H), 7.25 (2 H), 3.34 (2 H), 2.95 (4 H), 1.45 (9 H).

Intermediate 3

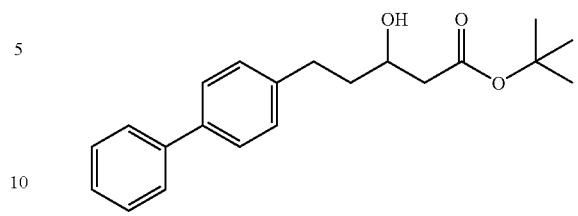

5-Biphenyl-4-yl-3-hydroxy-pentanoic acid tert-butyl ester

Sodium borohydride (51 mg, 1.4 mmol) was added in one portion to a stirred solution of 5-biphenyl-4-yl-3-oxo-pentanoic acid tert-butyl ester (Intermediate 2, 400 mg, 1.23 mmol) in methanol (5 mL) at 0° C. under nitrogen. Stirring was continued for 30 mrrinutes then 1 M hydrochloric acid (5 mL) was added. The crude reaction mixture was extracted with diethyl ether (3×20 mL) and the resulting organic phases were combined, dried (MgSO$_4$) then the solvent removed by evaporation under reduced pressure to give the title compound (375 mg, 93%) as a colourless oil. LC/MS: 3.67 min; z/e 344, calcd (M+NH$_4$) 344. $^1$H NMR (400 MHz: CDCl$_3$): 7.55 (2 H), 7.50 (2 H), 7.43 (2 H), 7.38 (3 H), 4.01 (1 H), 3.25 (1 H), 2.80 (2 H), 2.44 (2 H), 1.82 (2 H), 1.45 (9 H).

Intermediate 4

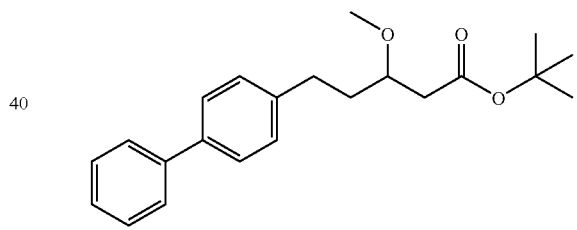

5-Biphenyl-4-yl-3-methoxy-pentanoic acid tert-butyl ester

Sodium hydride (60%; 7.0 mg, 0.17 mmol) was added to a stirred solution of 5-biphenyl-4-yl-3-hydroxy-pentanoic acid tert-butyl ester (Intermediate 3, 50 mg, 0.15 mmol) in dimethylformamide (0.5 mL) at 0° C. under nitrogen. After stirring for 5 minutes methyl iodide (14 µL, 0.23 mmol) was added and stirring continued for 12 hours. The volatiles were evaporated under reduced pressure and the residue partitioned between dichloromethane (5 mL) and water (5 mL). The phases were separated and the organic phase dried (MgSO$_4$), then the solvent evaporated. The residue was purified by column chromatography on silica gel (1:8 diethyl ether:cyclohexane) to give the title compound (18 mg, 35%) as a colourless gum. LC/MS: 3.87 min; z/e 358, calcd (M+NH$_4$) 358. $^1$H NMR (400 MHz: CDCl$_3$): 7.59 (2 H), 7.53 (2 H), 7.42 (2 H), 7.28 (3 H), 3.68 (1 H), 3.40 (3 H), 2.77 (2 H), 2.56 (1 H), 2.38 (1 H), 1.88 (2 H), 1.47 (9 H).

Intermediate 5

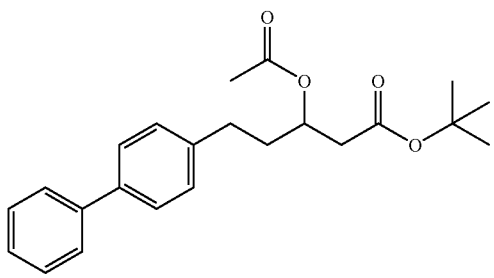

3-Acetoxy-5-biphenyl-4-yl-pentanoic acid tert-butyl ester

Acetic anhydride (40 μL, 0.42 mmol) was added to a stirred solution of 5-biphenyl-4-yl-3-hydroxy-pentanoic acid tert-butyl ester (Intermediate 3, 54 mg, 0.17 mmol), 4-dimethylaminopyridine (5.0 mg, 41 μmol) and pyridine (54 μL, 0.66 mol) in dichloromethane (1 mL) at room temperature under nitrogen. Stirring was continued for 12 hours at room temperature before the addition of 2 M hydrochloric acid (5 mL) and dichloromethane (5 mL). The phases were separated and aqueous phase extracted with dichloromethane (3×5 mL). The organic phases were combined, washed with brine (5 mL) and dried (MgSO$_4$). The solvent was removed by evaporation under reduced pressure to give the title compound (45 mg, 74%) as a colourless gum. LC/MS: 3.91 min; z/e 386, calcd (M+NH$_4$) 386. $^1$H NMR (400 MHz: CDCl$_3$): 7.59 (2 H), 7.52 (2 H), 7.42 (2 H), 7.33 (1 H), 7.25 (2 H), 5.29 (1 H), 2.70 (2 H), 2.53 (2 H), 2.05 (3 H), 1.97 (2H), 1.42 (9 H).

Intermediate 6

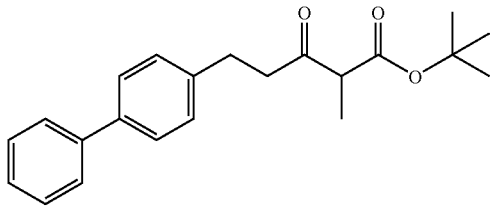

5-Biphenyl-4-yl-2-methyl-3-oxo-pentanoic acid tert-butyl ester

A solution of 5-biphenyl4-yl-3-oxo-pentanoic acid tert-butyl ester (Intermediate 2, 0.30 g, 0.93 mmol) in dimethyl formamide (1.5 mL) was added to a suspension of sodium hydride (60%; 38 mg, 0.94 mmol) in dimethyl formamide (1 mL) at 0° C. under nitrogen. After stirring for 20 minutes methyl iodide (58 μL, 0.93 mmol) was added and the reaction warmed to room temperature at which stirring was continued for 2 hours. 0.5 M Hydrochloric acid (5 mL) was added and the quenched reaction mixture extracted with diethyl ether (3×5 mL). The organic phases were combined, washed with brine (5 mL) and dried (MgSO$_4$). The volatiles were removed by evaporation under reduced pressure and the residue was purified by column chromatography on silica gel (1:6 diethyl ether: 40–60 petroleum ether) to give the title compound (163 mg, 52%) as a colourless oil. LC/MS: 3.81 min; z/e 356, calcd (M+NH$_4$) 356. $^1$H NMR (400 MHz: CDCl$_3$): 7.59 (2 H), 7.51 (2 H), 7.42 (2 H), 7.32 (1 H), 7.22 (2 H), 3.42 (1 H), 2.97 (3 H), 2.83 (1 H), 1.42 (9 H), 1.28 (3 H).

Intermediate 7

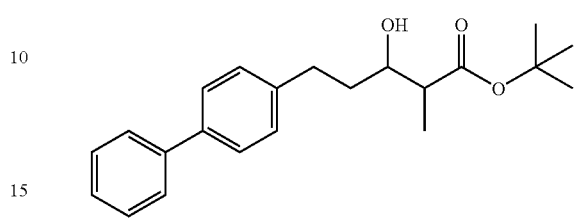

5-Biphenyl-4-yl-3-hydroxy-2-methyl-pentanoic acid tert-butyl ester

Sodium borohydride (17 mg, 0.44 mmol) was added to a stirred solution of 5-biphenyl-4-yl-2-methyl-3-oxo-pentanoic acid tert-butyl ester (Intermediate 6, 135 mg, 0.399 mmol) in methanol (3 mL) at 0° C. under nitrogen. After stirring for 1 hour 1 M hydrochloric acid (5 mL) was added and the crude reaction mixture extracted with diethyl ether (3×5 mL). The organic phases were combined, washed with brine (5 mL) and dried (MgSO$_4$). The volatiles were removed by evaporation under reduced pressure to give the title compound (130 mg, 96%) as a colourless gum, mixture of diastereoisomers. LC/MS: 3.72 min; z/e 341, calcd (M+1) 341.$^1$H NMR (400 MHz: CDCl$_3$): 7.59 (2 H), 7.51 (2 H), 7.42 (2 H), 7.28 (3 H), 4.21, 3.90, 3.65, 2.89, 2.75, 1.81, 1.69, 1.55, 1.44, 1.30, 1.18.

Intermediate 8

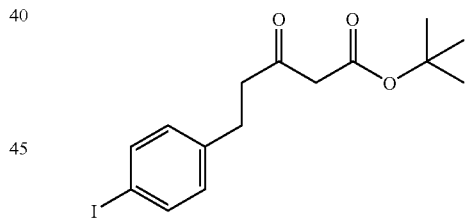

5-(4-Iodo-phenyl)-3-oxo-pentanoic acid tert-butyl ester t-butylacetoacetate (1.5 mL, 9.2 mmol) was added dropwise over 2 minutes to a stirred suspension of sodium hydride (60%; 400 mg, 10.0 mmol) in tetrahydrofuran at 0° C. under nitrogen. After stirring for 10 minutes n-butyl lithium in hexane (1.6 M; 6.0 mL, 9.6 mmol) was added then stirring continued for a further ten minutes. The resulting solution was treated dropwise with a solution of 4-iodobenzyl bromide (2.97 g, 10.0 mmol) in tetrahydrofuran (4 mL) and then warmed to room temperature. The reaction was stirred for 40 minutes at room temperature and then quenched with 6 M HCl (5 mL). The resulting mixture was extracted with diethyl ether (3×50 mL). The organic phases were combined, washed with brine (50 mL) and dried (MgSO$_4$) then the solvent evaporated under reduced pressure. The residue was purified via flash chromatography on silica gel (1:20 to 1:10 ethyl acetate/cyclohexane) to give the title compound (1.88 g, 54%) as a yellow oil. LC/MS: 3.66 min; z/e 375, calcd (M+1) 375. $^1$H NMR (400 MHz; CDCl$_3$): 7.6 (2 H), 6.93 (2 H), 3.33 (2 H), 2.85 (4 H), 1.45 (9 H).

Intermediate 9

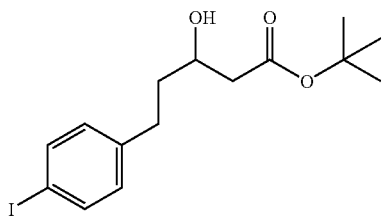

3-Hydroxy-5-(4-iodo-phenyl)-pentanoic acid tert-butyl ester

Sodium borohydride (198 mg, 5.20 mmol) was added in one portion to a stirred solution of 5-(4-iodo-phenyl)-3-oxo-pentanoic acid tert-butyl ester (Intermediate 8, 1.78 g, 4.76 mmol) in methanol (15 mL) at 0° C. The reaction was stirred for 20 minutes then quenched with 1 M HCl (15 mL). The resulting mixture was extracted with diethyl ether (3×20 mL). The organic phases were combined, dried (MgSO$_4$) then the solvent removed by evaporation under reduced pressure to give the title compound (1.46 g, 82%) as a colourless oil. LC/MS: 3.59 min; z/e 394, calcd (M+NH$_4$) 394. $^1$H NMR (400 MHz: CDCl$_3$): 7.6 (2 H), 6.95 (2 H), 3.95 (1 H), 2.7 (2 H), 2.38 (2 H), 1.73 (2 H), 1.45 (9 H).

Intermediate 10

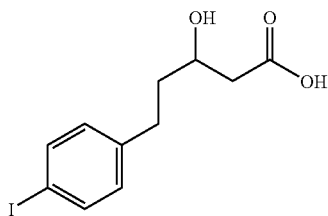

3-Hydroxy-5-(4-iodo-phenyl)-pentanoic acid

Silica gel (19 g) was added to a stirred solution of 3-hydroxy-5-(4-iodo-phenyl)-pentanoic acid tert-butyl ester (Intermediate 9, 1.2 g, 3.2 mmol) in toluene (100 mL) and the resulting suspension heated at reflux for 5.5 hours. The reaction was cooled to room temperature and then filtered through a thin pad of celite, washing with 20% methanol/dichloromethane (2×50 mL). The filtrate was evaporated under reduced pressure to give the title compound (586mg, 57%) as a white solid. LC/MS: 3.01 min; z/e 319, calcd (M−1) 319. $^1$H NMR (400 MHz: DMSO-d$_6$): 7.63 (2 H), 7.00 (2 H), 3.77 (1 H), 2.60 (2 H), 2.3 (2 H), 1.62 (2 H).

What is claimed is:

1. A compound of formula (Ia):

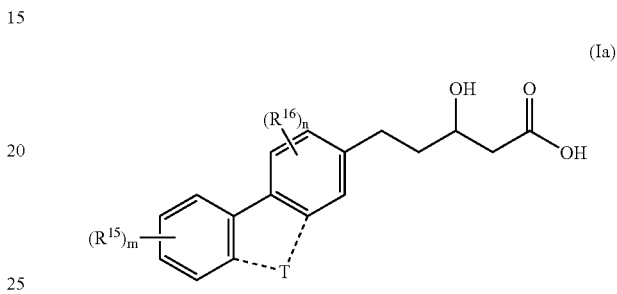

(Ia)

wherein:

T is absent or represents O, S, NR$^{17}$ or CR$^{17}$ R$^{18}$;

— represents optional bonds;

R$^{15}$ and R$^{16}$ each independently represents halo, cyano, nitro, OR$^{17}$, SR$^{17}$, COR$^{17}$, NR$^{18}$COR$^{17}$, CONR$^{17}$R$^{18}$, optionally substituted phenoxy or C$_{1-6}$ alkyl optionally substituted by OR$^{17}$;

R$^{17}$ represents H, C$_{1-6}$ alkyl or C$_{1-4}$ alkylaryl;

R$^{18}$ represents H or C$_{1-6}$alkyl;

m and n each independently represents 0 or an integer 1, 2 or 3;

with the proviso that when T is absent, R$^{15}$ does not represent NR$^{18}$COR$^{17}$or CONR$^{17}$R$^{18}$ in the ortho position; and physiologically functional derivatives thereof.

2. A method for the treatment of a human or animal subject suffering from an autoimmune disorder or an inflammatory condition which method comprises administering to said human or animal subject an effective amount of a compound as claimed in claim 1.

3. A pharmaceutical composition comprising a compound as claimed in claim 1 and a pharmaceutically acceptable carrier therefor, and optionally one or more other therapeutic agents.

* * * * *